(12) United States Patent
Baniecki et al.

(10) Patent No.: US 11,098,411 B2
(45) Date of Patent: Aug. 24, 2021

(54) OXYGEN GENERATING ELECTRODE AND OXYGEN GENERATOR

(71) Applicant: FUJITSU LIMITED, Kawasaki (JP)

(72) Inventors: John David Baniecki, Zama (JP); Hiroyuki Aso, Atsugi (JP); Yoshihiko Imanaka, Atsugi (JP)

(73) Assignee: FUJITSU LIMITED, Kawasaki (JP)

( * ) Notice: Subject to any disclaimer, the term of this patent is extended or adjusted under 35 U.S.C. 154(b) by 252 days.

(21) Appl. No.: 16/445,536

(22) Filed: Jun. 19, 2019

(65) Prior Publication Data

US 2019/0301030 A1    Oct. 3, 2019

Related U.S. Application Data

(63) Continuation of application No. PCT/JP2017/046497, filed on Dec. 25, 2017.

(30) Foreign Application Priority Data

Jan. 6, 2017 (JP) .............................. JP2017-001160

(51) Int. Cl.

| C25B 11/095 | (2021.01) |
| C01G 53/00 | (2006.01) |
| C25B 1/04 | (2021.01) |
| C25B 11/03 | (2021.01) |
| C25B 9/00 | (2021.01) |
| C25B 11/04 | (2021.01) |

(Continued)

(52) U.S. Cl.
CPC ............ *C25B 11/095* (2021.01); *C01G 53/70* (2013.01); *C25B 1/04* (2013.01); *C25B 9/00* (2013.01); *C25B 11/03* (2013.01); *C25B 11/031* (2021.01); *C25B 11/04* (2013.01); *C01P 2002/34* (2013.01); *C07C 229/24* (2013.01); *Y02E 60/36* (2013.01)

(58) Field of Classification Search
CPC ....... C25B 11/095; C25B 1/04; C25B 11/085; C25B 11/051; C25B 11/048; C25B 11/04
See application file for complete search history.

(56) References Cited

U.S. PATENT DOCUMENTS

| 5,944,966 A | 8/1999 | Suetsugu et al. |
| 2013/0020207 A1 | 1/2013 | Shao-Horn et al. |

(Continued)

FOREIGN PATENT DOCUMENTS

| JP | 8-325775 A | 12/1996 |
| JP | 11-172483 A | 6/1999 |

(Continued)

OTHER PUBLICATIONS

Amino Acid (https://en.wikipedia.org/wiki/Amino_acid#:~:text=Amino%20acids%20are%20the%20structural,called%20either%20polypeptides%20or%20proteins.) (Year: 2021).*

(Continued)

*Primary Examiner* — Nicholas A Smith
(74) *Attorney, Agent, or Firm* — Westerman, Hattori, Daniels & Adrian, LLP

(57) ABSTRACT

An oxygen generating electrode includes: an oxide film having a perovskite structure; an organic film over the oxide film; and a conductive film electrically coupled to the organic film, wherein the organic film contains an amino acid having a side chain of negative polarity.

14 Claims, 7 Drawing Sheets

(51) Int. Cl.
*C25B 11/031* (2021.01)
*C07C 229/24* (2006.01)

(56) References Cited

U.S. PATENT DOCUMENTS

2016/0376717 A1 12/2016 Tamura et al.
2017/0211193 A1 7/2017 Miyazaki et al.

FOREIGN PATENT DOCUMENTS

| JP | 2015-175020 A | 10/2015 |
| JP | 2016-33257 A | 3/2016 |

OTHER PUBLICATIONS

International Search Report dated Feb. 13, 2018, issued in counterpart International Application No. PCT/JP2017/046497 (2 pages).

* cited by examiner ated in the latter half reaction (Formula 2). Various proposals may be made for an oxygen generating electrode suitable for the latter half reaction (Formula 2).

OXYGEN GENERATING ELECTRODE AND OXYGEN GENERATOR

CROSS-REFERENCE TO RELATED APPLICATION

This application is a continuation application of International Application PCT/JP2017/046497 filed on Dec. 25, 2017 and designated the U.S., the entire contents of which are incorporated herein by reference. The International Application PCT/JP2017/046497 is based upon and claims the benefit of priority of the prior Japanese Patent Application No. 2017-001160, filed on Jan. 6, 2017, the entire contents of which are incorporated herein by reference.

FIELD

The embodiments discussed herein are related to an oxygen generating electrode and an oxygen generator.

BACKGROUND

Techniques for generating oxygen gas through the decomposition of water have been studied.

Japanese Laid-open Patent Publication Nos. 2015-175020 and 11-172483 are disclosed as related art.

SUMMARY

According to an aspect of the embodiments, an oxygen generating electrode includes: an oxide film having a perovskite structure; an organic film over the oxide film; and a conductive film electrically coupled to the organic film, wherein the organic film contains an amino acid having a side chain of negative polarity.

The object and advantages of the invention will be realized and attained by means of the elements and combinations particularly pointed out in the claims.

It is to be understood that both the foregoing general description and the following detailed description are exemplary and explanatory and are not restrictive of the invention.

DESCRIPTION OF EMBODIMENTS

The decomposition reaction of water consists of a combination of the following half reactions, and oxygen gas is

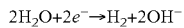      (Formula 1)

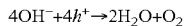      (Formula 2)

However, it me be difficult to generate oxygen gas with high efficiency using an existing oxygen generating electrode.

For example, an oxygen generating electrode and an oxygen generator that generate oxygen gas with high efficiency may be provided.

Embodiments will be specifically described below with reference to the accompanying drawings.

First Embodiment

Figure 1:
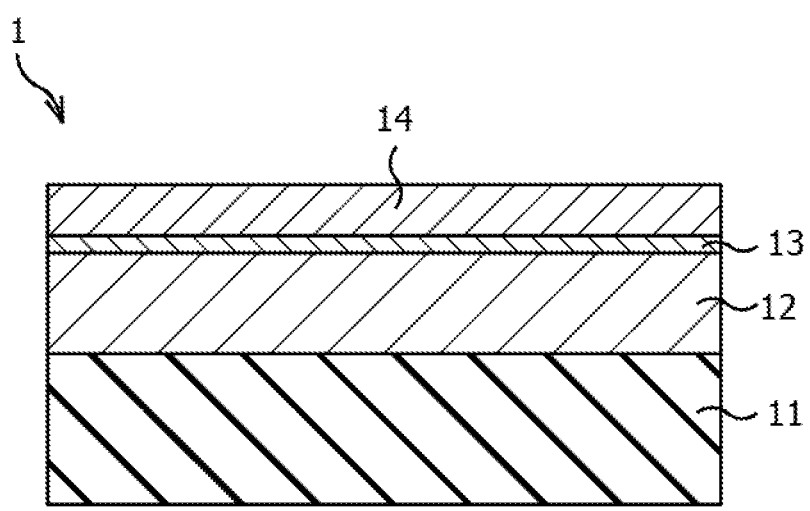
FIG. 1 is a sectional view illustrating a configuration of an oxygen generating electrode according to a first embodiment.

First, a first embodiment will be described. The first embodiment is an exemplary oxygen generating electrode. FIG. 1 is a sectional view illustrating a configuration of the oxygen generating electrode according to the first embodiment.

As illustrated in FIG. 1, an oxygen generating electrode 1 according to the first embodiment includes an oxide film 12 having a perovskite structure, an organic film 13 on the oxide film 12, and a conductive film 14 electrically coupled to the organic film 13. The organic film 13 contains an amino acid having a side chain of negative polarity. For example, the oxide film 12 is formed on a substrate 11 having insulating properties, and the conductive film 14 is formed on the organic film 13.

The oxide film 12 having a perovskite structure exhibits high activity for the half reaction of Formula 2 in which oxygen gas is generated. The organic film 13 contains an amino acid, and a carboxyl group contained in a main chain of the amino acid has a low acid dissociation constant pKa. For this reason, the organic film 13 promotes the donation of protons ($h^+$) in the half reaction of Formula 2. Therefore, according to the present embodiment, oxygen gas may be generated with excellent efficiency.

The side chain of negative polarity is strongly bonded to the oxide film 12. Therefore, the oxygen generating electrode may be used stably over a long period of time, and may have excellent reliability. Examples of the amino acid having a side chain of negative polarity include L-glutamic acid and aspartic acid. A carboxyl group contained in a main chain of L-glutamic acid has an acid dissociation constant pKa of about 2.16, and a carboxyl group contained in a main chain of aspartic acid has an acid dissociation constant pKa of about 1.95.

For example, the substrate 11 is an undoped MgO substrate or an undoped $SrTiO_3$ substrate. For example, an oxide having a perovskite structure contained in the oxide film 12 has a chemical formula represented by $ANiO_{3-\delta}$. A is, for example, Pr, La, Sm, Nd, Gd or Eu or any combination thereof, and is preferably Pr. The value of δ is, for example, greater than 0 and less than 0.5. The oxide film 12 has a thickness of, for example, 10 nm to 50 nm. The organic film 13 contains, for example, L-glutamic acid or aspartic acid or both of them. For example, the organic film 13 preferably contains L-glutamic acid. The organic film 13 has a thickness of, for example, 1 nm to 5 nm. The conductive film 14 is, for example, a porous Au film having a thickness of 5 nm to 20 nm.

In one example, the oxide film 12 is a 50 nm-thick $PrNiO_3$ film, the organic film 13 is a 5 nm-thick L-glutamic acid film, and the conductive film 14 is a 15 nm-thick porous Au film. In another example, the oxide film 12 is a 50 nm-thick $PrNiO_3$ film, the organic film 13 is a 1 nm-thick L-glutamic acid film, and the conductive film 14 is a 15 nm-thick porous Au film. In yet another example, the oxide film 12 is a 50 nm-thick $LaNiO_3$ film, the organic film 13 is a 5 nm-thick L-glutamic acid film, and the conductive film 14 is a 15 nm-thick porous Au film.

Next, an example of a method for manufacturing the oxygen generating electrode 1 according to the first embodiment will be described. In this example, first, the oxide film 12 is formed on the substrate 11 by a pulsed laser deposition (PLD) process. Next, the organic film 13 is formed on the oxide film 12 by a vapor deposition process. An apparatus suitable for forming the organic film 13 will be described later. Thereafter, the conductive film 14 is formed on the organic film 13 by a vapor deposition process.

Figure 2:
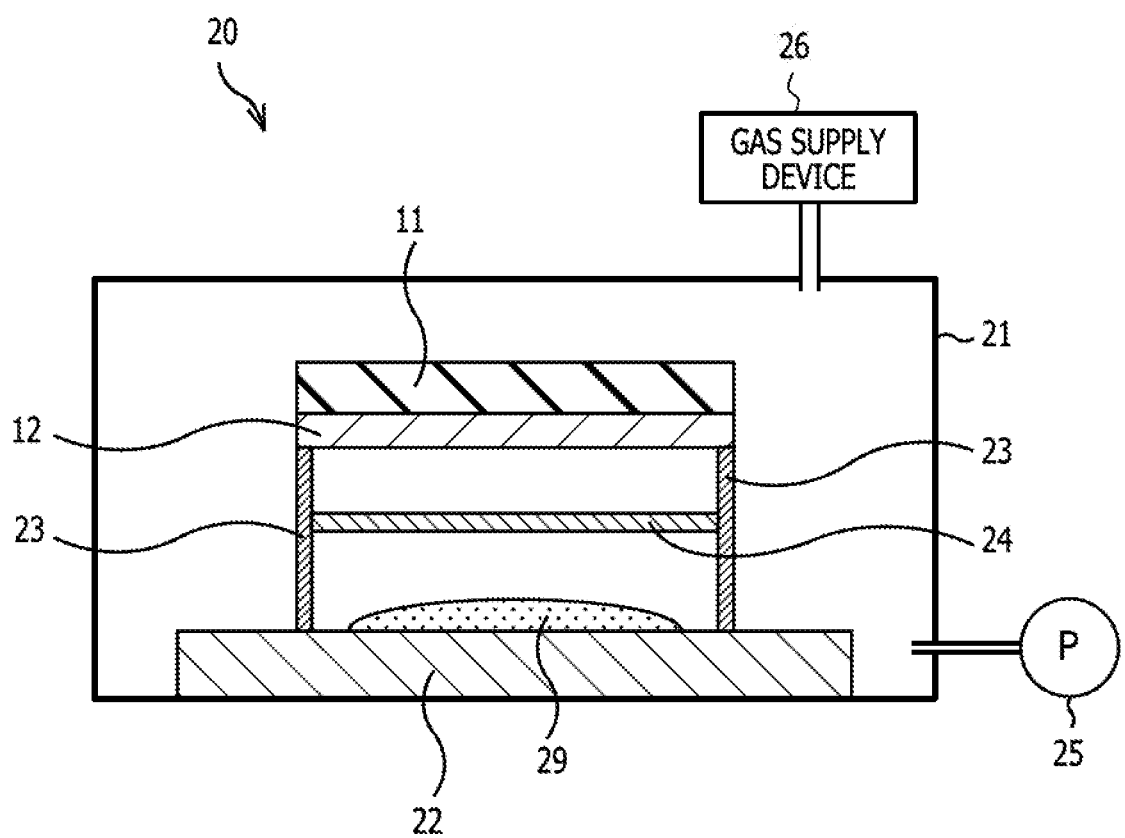
FIG. 2 is a schematic view illustrating a film forming apparatus suitable for forming an organic film.

FIG. 2 is a schematic view illustrating a film forming apparatus suitable for forming the organic film 13. As illustrated in FIG. 2, a film forming apparatus 20 includes a chamber 21, a heater 22 in the chamber 21, and a support 23 that is provided above the heater 22 and supports the substrate 11 and the oxide film 12. To the chamber 21, a pump 25 and a gas supply device 26 are coupled. On the heater 22, a raw material powder 29 of the organic film 13 is placed, and the oxide film 12 is placed on the support 23 so as to face the raw material powder 29. Preferably, a mesh 24 is disposed between the raw material powder 29 and the oxide film 12.

In forming the organic film 13 using the film forming apparatus 20, for example, the raw material powder 29 is heated by the heater 22 with an inert gas such as nitrogen gas being supplied from the gas supply device 26 into the chamber 21 and the pressure in the chamber 21 being adjusted by the pump 25. The heated raw material powder 29 is vaporized and reaches the surface of the oxide film 12 through the openings of the mesh 24 to form the organic film 13 on the oxide film 12.

Figure 3:
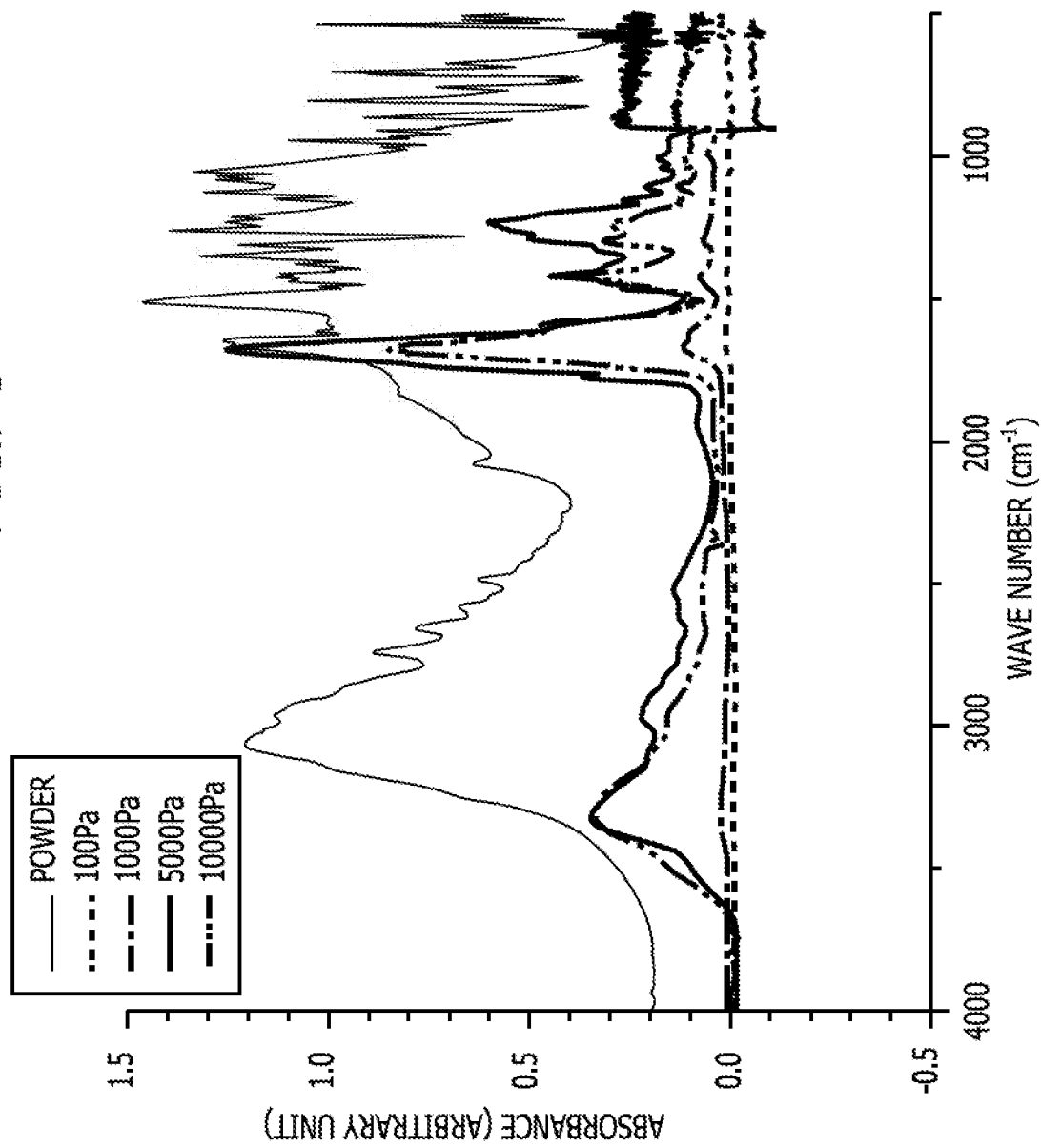
FIG. 3 is a diagram illustrating analysis results of organic films and a glutamic acid powder.

Here, the analysis results of the organic film 13 formed using the film forming apparatus 20 will be described. Film formation was performed at 5000 Pa and 210° C. for 5 minutes using 0.025 g of a glutamic acid powder as the raw material powder 29, and then the resulting film was cooled at 1000 Pa. Nitrogen gas was supplied into the chamber 21. A MgO substrate was used as the substrate 11, and a 15 nm-thick $PrNiO_3$ film was used as the oxide film 12. The organic film 13 was analyzed by Fourier transform infrared spectroscopy (FT-IR). The analysis results of the organic film 13 are illustrated in FIG. 3. As illustrated in FIG. 3, a peak of amide I was observed at a wave number of 1690 $cm^{-1}$ to 1600 $cm^{-1}$, and a peak of amide II was observed at a wave number of 1520 $cm^{-1}$ to 1550 $cm^{-1}$. This indicates that a film of β-glutamic add was formed. For reference, FIG. 3 also illustrates the analysis results of the glutamic add powder as well as the analysis results of organic films formed from the glutamic acid powder with the pressure in the chamber 21 being adjusted to 100 Pa, 1000 Pa or 10000 Pa.

Second Embodiment

Figure 4:
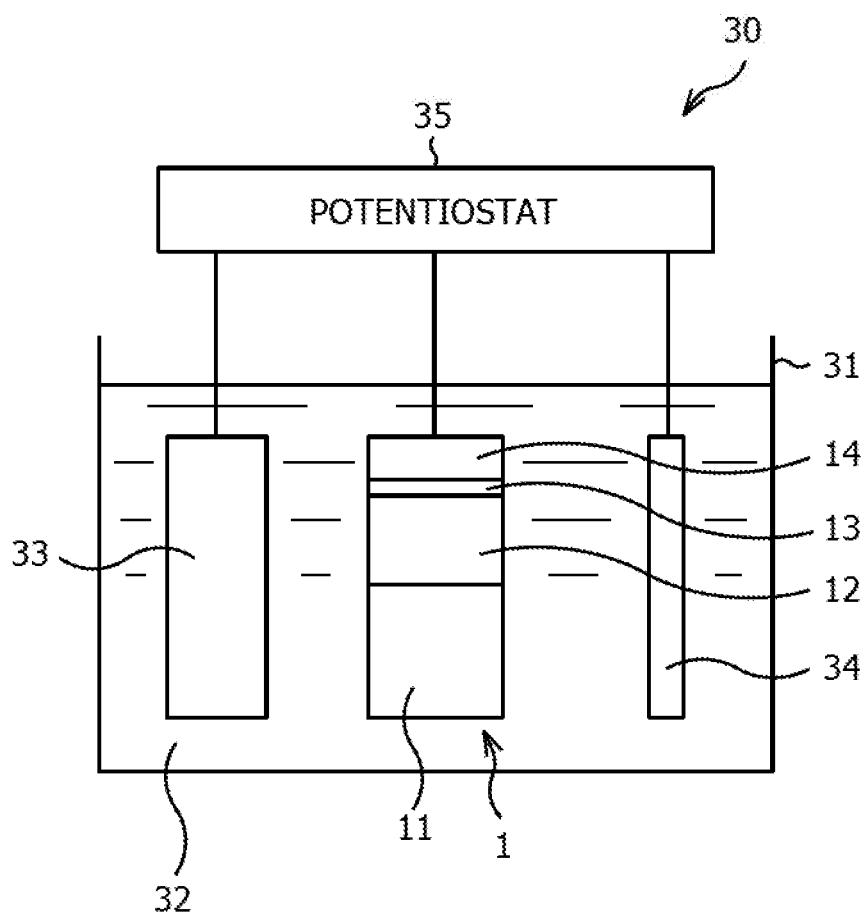
FIG. 4 is a drawing illustrating a configuration of an oxygen generator according to a second embodiment.

Next, a second embodiment will be described. The second embodiment relates to an oxygen generator including the oxygen generating electrode 1. FIG. 4 is a drawing illustrating a configuration of the oxygen generator according to the second embodiment.

As illustrated in FIG. 4, an oxygen generator 30 according to the second embodiment includes an aqueous electrolyte solution 32 contained in a tank 31, the oxygen generating electrode 1, a reference electrode 33 and a counter electrode 34 in the aqueous electrolyte solution 32, and a potentiostat 35 connected to the oxygen generating electrode 1, the reference electrode 33 and the counter electrode 34. For example, the reference electrode 33 is an Ag/AgCl electrode, the counter electrode 34 is a Pt electrode, and the aqueous electrolyte solution 32 is a 0.5 M to 2.0 M aqueous KOH solution.

In the oxygen generator 30, the oxygen generating electrode 1 is used as a working electrode. Therefore, adjusting the potential of the oxygen generating electrode 1 with respect to the reference electrode 33 leads to generation of oxygen gas with high efficiency.

Figure 5A:
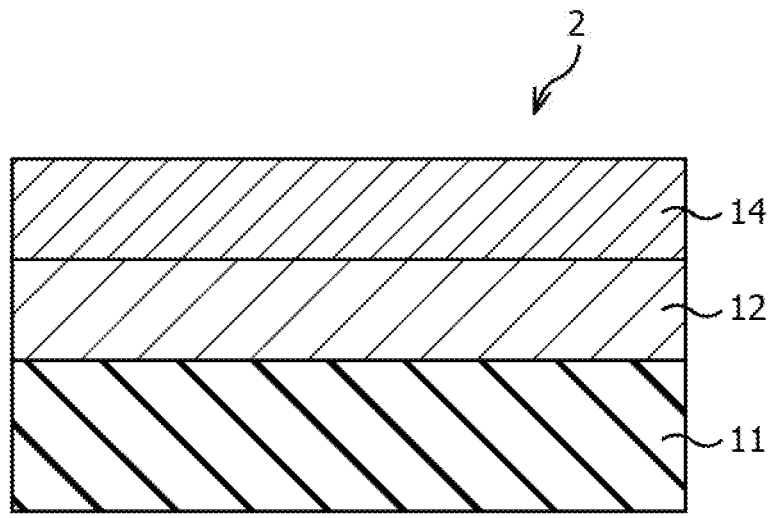
FIG. 5A is a sectional view illustrating a configuration of an oxygen generating electrode.

Here, an experiment on the oxygen generator 30 conducted by the present inventors will be described. In this experiment, the current flowing between the oxygen generating electrode 1 and the counter electrode 34 was measured at various potentials of the oxygen generating electrode 1 with respect to the reference electrode 33. For reference, the same measurement was conducted also for an oxygen generating apparatus including an oxygen generating electrode 2 of a reference example illustrated in FIG. 5A in place of the oxygen generating electrode 1. The oxygen generating electrode 2 of the reference example includes the substrate 11, the oxide film 12 and the conductive film 14, but does not include the organic film 13. The measurement results of the oxygen generators are illustrated in FIG. 5B.

Figure 5B:
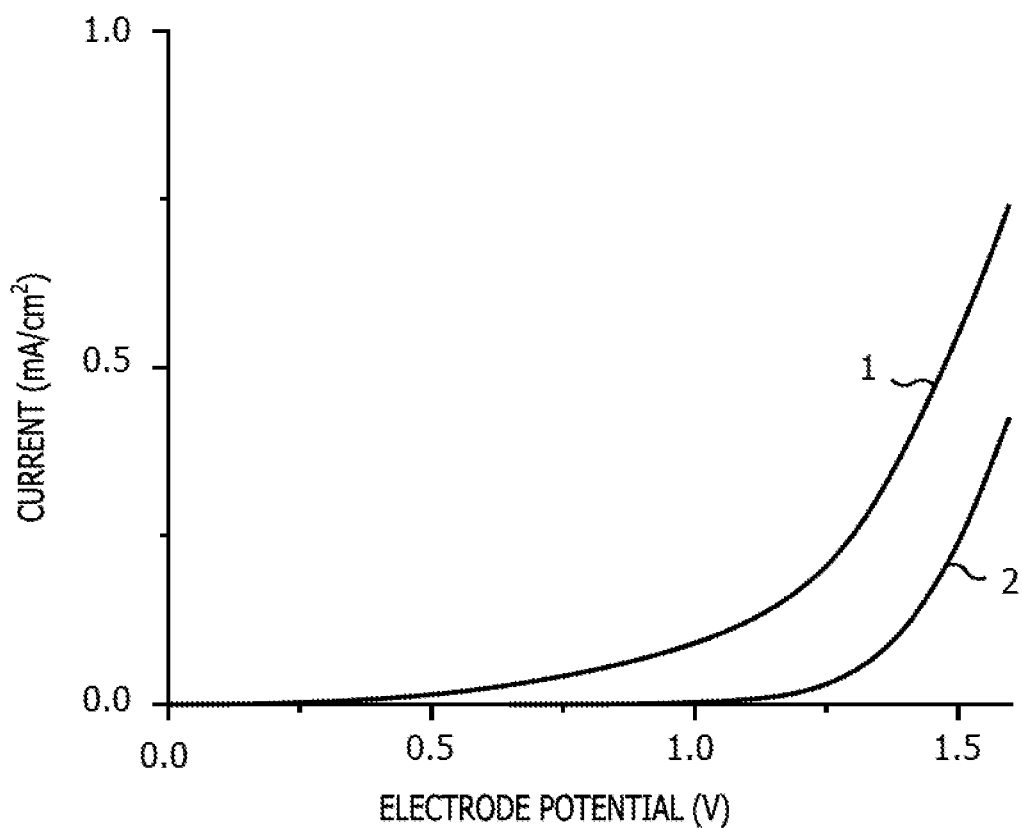
FIG. 5B is a diagram illustrating a relationship between electrode potential and current.

As illustrated in FIG. 5B, in the oxygen generator 30 including the oxygen generating electrode 1, a current larger than that of the oxygen generator including the oxygen generating electrode 2 flowed. For example, at a potential of the oxygen generating electrode 1 with respect to the reference electrode 33 of 1.25 V, a current four times as large as that of the oxygen generator including the oxygen generating electrode 2 flowed in the oxygen generator 30. This means that the oxygen generator 30 may generate oxygen gas with high efficiency.

Third Embodiment

Figure 6:
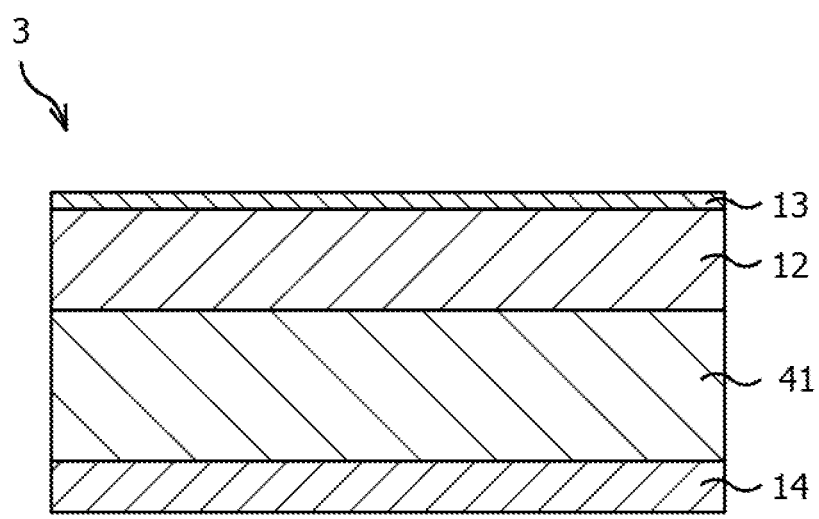
FIG. 6 is a sectional view illustrating a configuration of an oxygen generating electrode according to a third embodiment.

Next, a third embodiment will be described. The third embodiment is an exemplary oxygen generating electrode. FIG. 6 is a sectional view illustrating a configuration of the oxygen generating electrode according to the third embodiment.

As illustrated in FIG. 6, an oxygen generating electrode 3 according to the third embodiment includes an oxide film 12 having a perovskite structure, an organic film 13 on the oxide film 12, and a conductive film 14 electrically connected to the organic film 13. The organic film 13 contains an amino acid having a side chain of negative polarity. For example, the oxide film 12 is formed on a substrate 41 having conductive properties, and the conductive film 14 is formed on a back surface of the substrate 41.

The oxygen generating electrode 3 according to the third embodiment provides the same effect as that of the first embodiment. For example, oxygen gas may be generated with excellent efficiency.

Fourth Embodiment

Figure 7:
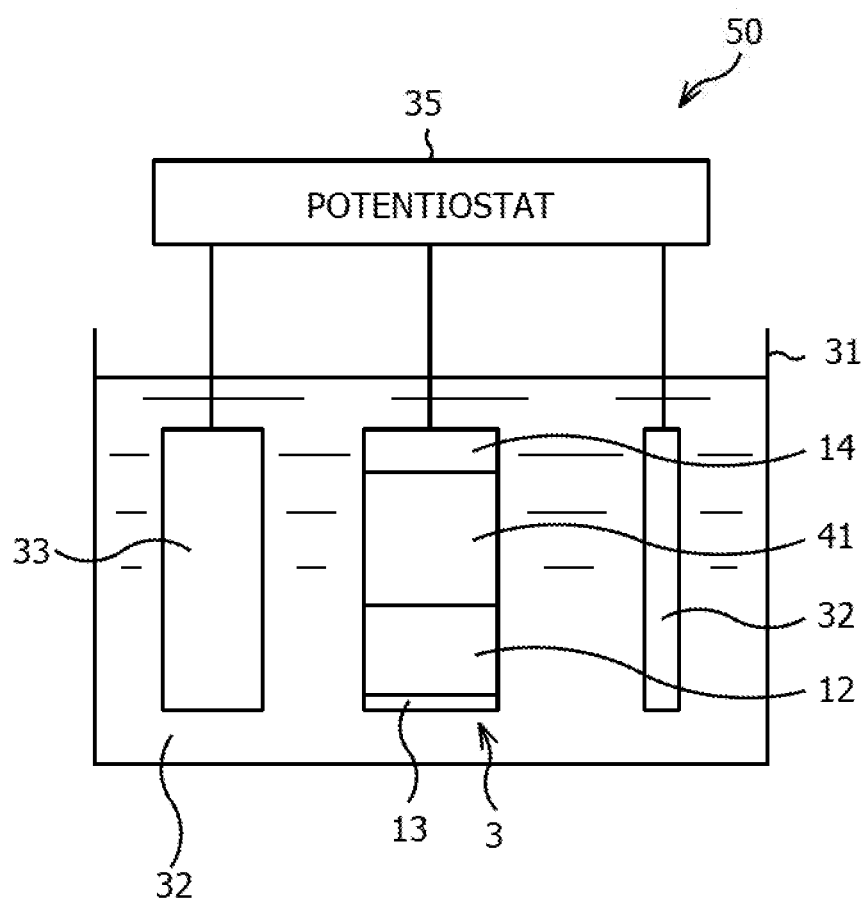
FIG. 7 is a drawing illustrating a configuration of an oxygen generator according to a fourth embodiment.

Next, a fourth embodiment will be described. The fourth embodiment relates to an oxygen generator including the oxygen generating electrode 3. FIG. 7 is a drawing illustrating a configuration of the oxygen generator according to the fourth embodiment.

As illustrated in FIG. 7, an oxygen generator 50 according to the fourth embodiment includes the oxygen generating electrode 3 in place of the oxygen generating electrode 1 in the second embodiment. The oxygen generator 50 has the same configuration as that of the second embodiment in other respects.

In the oxygen generator 50, the oxygen generating electrode 3 is used as a working electrode. Therefore, adjusting the potential of the oxygen generating electrode 3 with respect to the reference electrode 33 leads to generation of oxygen gas with high efficiency.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. An oxygen generating electrode comprising:
   an oxide film having a perovskite structure;
   an organic film over the oxide film; and
   a conductive film electrically coupled to the organic film,
   wherein the organic film contains an amino acid having a side chain of negative polarity.

2. The oxygen generating electrode according to claim 1, wherein the amino acid is L-glutamic acid.

3. The oxygen generating electrode according to claim 1, wherein the conductive film is a porous Au film.

4. The oxygen generating electrode according to claim 1, wherein the oxide film contains an oxide represented by a chemical formula $ABO_{3-\delta}$
   wherein A is a metal element having a valence of 3 or 4, and
   B is Ni.

5. The oxygen generating electrode according to claim 4, wherein A is Pr, La, Sm, Nd, Gd, Eu or any combination of Pr, La, Sm, Nd, Gd and Eu.

6. The oxygen generating electrode according to claim 4, wherein $\delta$ has a value greater than 0 and less than 0.5.

7. The oxygen generating electrode according to claim 4, wherein the oxide film contains $PrNiO_3$.

8. An oxygen generator comprising:
   an aqueous electrolyte solution;
   an oxygen generating electrode in the aqueous electrolyte solution;
   a reference electrode and a counter electrode in the aqueous electrolyte solution; and
   a potentiostat connected to the oxygen generating electrode, the reference electrode and the counter electrode,
   wherein the oxygen generating electrode includes:
   an oxide film having a perovskite structure;
   an organic film which is provided over the oxide film and contains an amino acid having a side chain of negative polarity; and
   a conductive film electrically coupled to the organic film.

9. The oxygen generator according to claim 8, wherein the amino acid is L-glutamic acid.

10. The oxygen generator according to claim 8, wherein the conductive film is a porous Au film.

11. The oxygen generator according to claim 8,
    wherein the oxide film contains an oxide represented by a chemical formula $ABO_{3-\delta}$
    wherein A is a metal element having a valence of 3 or 4, and
    B is Ni.

12. The oxygen generator according to claim 11, wherein A is Pr, La, Sm, Nd, Gd, Eu or any combination of Pr, La, Sm, Nd, Gd and Eu.

13. The oxygen generator according to claim 11, wherein $\delta$ has a value greater than 0 and less than 0.5.

14. The oxygen generator according to claim 11, wherein the oxide film contains $PrNiO_3$.

* * * * *